(12) United States Patent
Nakajima et al.

(10) Patent No.: US 9,109,982 B2
(45) Date of Patent: Aug. 18, 2015

(54) SLICED SPECIMEN PREPARING APPARATUS

(75) Inventors: Daisuke Nakajima, Neyagawa (JP); Yuko Nanjo, Neyagawa (JP)

(73) Assignee: KURASHIKI BOSEKI KABUSHIKI KAISHA, Okayama (JP)

( * ) Notice: Subject to any disclaimer, the term of this patent is extended or adjusted under 35 U.S.C. 154(b) by 0 days.

(21) Appl. No.: 14/113,951

(22) PCT Filed: Apr. 24, 2012

(86) PCT No.: PCT/JP2012/060953
§ 371 (c)(1),
(2), (4) Date: Oct. 25, 2013

(87) PCT Pub. No.: WO2012/147731
PCT Pub. Date: Nov. 1, 2012

(65) Prior Publication Data
US 2014/0051158 A1  Feb. 20, 2014

(30) Foreign Application Priority Data
Apr. 26, 2011  (JP) .................................. 2011-098483

(51) Int. Cl.
*G01N 1/28* (2006.01)
*G01N 1/06* (2006.01)

(52) U.S. Cl.
CPC . *G01N 1/286* (2013.01); *G01N 1/06* (2013.01)

(58) Field of Classification Search
CPC ............ G01N 1/06; G01N 1/286; G01N 1/04
USPC ............... 422/536, 82.05; 435/288.7
See application file for complete search history.

(56) References Cited

U.S. PATENT DOCUMENTS 6,330,348 B1 * 12/2001 Kerschmann et al. ......... 382/128
8,074,547 B2 * 12/2011 Ito et al. .......................... 83/76.8

(Continued)

FOREIGN PATENT DOCUMENTS

EP  1903325  *  9/2007
JP  6-265452    9/1994

(Continued)

OTHER PUBLICATIONS

English translation of International Preliminary Report on Patentability issued Nov. 7, 2013 in International (PCT) Application No. PCT/JP2012/060953.

(Continued)

*Primary Examiner* — Brian R Gordon
(74) *Attorney, Agent, or Firm* — Wenderoth, Lind & Ponack, L.L.P.

(57) ABSTRACT

A sliced specimen preparing apparatus prepares a sliced specimen by slicing a surface of a specimen block in which a specimen is embedded in an embedding-substance. The apparatus includes: a cutter configured to slice the surface of the specimen block; a surface exposure determination unit configured to determine whether or not the area of a specimen portion on the surface of the specimen block is sufficient for the preparation of the sliced specimen; and a specimen block transporting unit configured to transport the specimen block between the surface exposure determination unit and the cutter. The surface exposure determination unit includes a humidifying unit configured to humidify the surface of the specimen block; an irradiating unit configured to irradiate the surface of the specimen block with light; an imaging unit configured to receive reflected light from the humidified surface of the specimen block which is irradiated from the irradiating unit to acquire image data; an image data processing unit configured to discriminate the specimen portion on the surface of the specimen block from the embedding-substance portion based on the image data acquired by the imaging unit; and a controller configured to control the imaging unit, the irradiating unit, and the image data processing unit, and to determine whether or not the area of the specimen portion on the surface of the specimen block, the specimen portion being acquired by the image data processing unit, is sufficient for the preparation of the sliced specimen.

4 Claims, 8 Drawing Sheets

(56) References Cited

U.S. PATENT DOCUMENTS

| | | |
|---|---|---|
| 2004/0035275 A1 | 2/2004 | Lihl et al. |
| 2007/0180965 A1* | 8/2007 | Ito et al. ............... 83/73 |
| 2007/0199418 A1 | 8/2007 | Ito |
| 2008/0072723 A1 | 3/2008 | Nakajima et al. |
| 2009/0137028 A1 | 5/2009 | Ito et al. |
| 2010/0118133 A1 | 5/2010 | Walter et al. |
| 2011/0303352 A1 | 12/2011 | Nakajima et al. |
| 2013/0078648 A1* | 3/2013 | Moehrle ............... 435/7.21 |
| 2013/0203105 A1* | 8/2013 | Murayama et al. ....... 435/29 |
| 2014/0186215 A1* | 7/2014 | Shinta et al. ........... 422/69 |

FOREIGN PATENT DOCUMENTS

| | | |
|---|---|---|
| JP | 8-164125 | 6/1996 |
| JP | 2000-117693 | 4/2000 |
| JP | 2004-28507 | 1/2004 |
| JP | 2004-37459 | 2/2004 |
| JP | 2007/212276 | 8/2007 |
| JP | 2007-212387 | 8/2007 |
| JP | 2008-20293 | 1/2008 |
| JP | 2008-76251 | 4/2008 |
| JP | 2009-150864 | 7/2009 |
| JP | 2010-44069 | 2/2010 |
| JP | 2010-185789 | 8/2010 |
| JP | 2010-185818 | 8/2010 |

OTHER PUBLICATIONS

International Search Report (ISR) issued Jul. 10, 2012 in International (PCT) Application No. PCT/JP2012/060953.

* cited by examiner

SLICED SPECIMEN PREPARING APPARATUS

TECHNICAL FIELD

This application claims the priority of Japanese Patent Application No. 2011-98483 filed in Japan on Apr. 26, 2011, the contents of which are hereby incorporated by reference.

The present invention relates to a sliced specimen preparing apparatus and a sliced specimen preparing method that prepare a sliced specimen used for physical and chemical specimen analysis, microscopic observation of biological specimens, and the like.

BACKGROUND ART

A microtome has been widely known as a device for preparing a sliced specimen used for physical and chemical specimen analysis, microscopic observation of biological specimens, and the like. The microtome slices a surface of a specimen block, which is obtained by embedding a biological specimen or the like in an embedding-substance such as paraffin, with a cutter to prepare a slice.

The slice prepared by use of the microtome is, for example, collected in a bath filled with a extending liquid such as water or hot water with a blush or paper to be extended out and then, is stuck to a slide glass with an adhesive liquid (for example, water). Alternatively, the slice is placed directly on the slide glass to which an adhesive is applied, and is extended out by heating of the slide glass and is stuck to the slide glass. With evaporation of the adhesive liquid, the slice stuck to the slide glass is tightly fixed to the slide glass, and is used as a sliced specimen for tissue observation.

When the surface of the specimen block is sliced to form the slice, for effective tissue observation, a specimen portion needs to be sufficiently present on the surface of the specimen block from which the slice is cut out. Thus, generally, the specimen block is roughly cut by a predetermined thickness and then, is sliced for acquiring the slice for tissue observation. Roughly cutting the surface of the specimen block before slicing for tissue observation is referred to as surface exposure.

To resolve inclination of the surface of the specimen block with respect to a cutting surface of a cutter, there have proposed a method and a device that use a floodlight projection part and line sensor, which are arranged along the thickness of the specimen block, and incline the surface of the specimen block such that the amount of light that the line sensor receives becomes maximum, and perform surface exposure of the specimen block at this position as described in Japanese Patent Laid-open Publication No. 2008-76251. The surface exposure in this case serves to match the inclination angle of the surface of the specimen block with the cutting surface of the cutter, and is the same as the surface exposure in this application in a broad sense: "to acquire the surface for slicing for tissue observation", but is different from the surface exposure in this application in a narrow sense: "to acquire the surface for effective tissue observation".

SUMMARY OF THE INVENTION

As described above, to "acquire the surface for effective tissue observation", that is, to cause a specimen as an analyte to be exposed on the surface of the specimen block, the surface of the specimen block has been roughly cut by a predetermined thickness to perform surface exposure.

However, even when the surface is roughly cut by the predetermined thickness, the specimen portion may not sufficiently appear on the surface of the specimen block, resulting in that the prepared sliced specimen may be unsuited for tissue observation. In such case, it can be found whether or not the area of the specimen portion is sufficient for tissue observation only after rough cutting, in turn, after preparation of the sliced specimen. Further, in the case where steps such as rough cutting and preparation of the slice are automated, to visually check the surface of the specimen block for each of rough cutting, the automated steps must be stopped, which is very inefficient.

A microtome provided with an observation device for the rough cutting step has been known as described in Japanese Patent Laid-open Publication No. 6-265452. An apparatus provided with an upward illuminating device, a downward illuminating device, and a specimen inside illuminating device, which each have an LED to irradiate specimen, has been also known as described in Japanese Patent Laid-open Publication No. 2004-37459.

However, in the device described in Japanese Patent Laid-open Publication No. 6-265452, control to determine the cut surface is not taken into consideration. Further, when the tissue is close to transparent or is small, no identifiable image can be acquired. Moreover, the device described in Japanese Patent Laid-open Publication No. 2004-37459 requires an adjusting operation by a skilled person in the case of the need for change in the cutting direction, which puts a large load on the operator.

There has been known a thin-slice preparing device that generates an image based on image data acquired by imaging an embedded block in a downward illumination system and an image based on image data acquired by imaging the embedded block in a diffused illumination system, displaying both the images in a superimposed state, and thinly cutting a certain surface as described in Japanese Patent Laid-open Publication No. 2008-20293 and Japanese Patent Laid-open Publication No. 2007-212387. However, it should be noted that the device only displays the superimposed images, and the operator must recognize the state of a biological specimen in the embedded block based on the images, and designate the cut surface. For this reason, as conventional, the operator requires some experience and thus bears a large burden.

There has been also known a thin-slice preparing device that includes an imaging optical system for vertically illuminating a cut surface of an embedded block from a light source and receiving reflected light from the cut surface, executing binarization processing based on luminance information in image data to create light and shade contrast data, and identifying a portion of the surface where a biological specimen is exposed based on the light and shade contrast data as described in Japanese Patent Laid-open Publication No. 2007-212276. That is, the exposed biological-specimen portion and an embedding-substance portion are identified from another based on the light and shade contrast data.

There has been also known a sliced specimen preparing method and device that discriminate a bright paraffin block surface with a dark segmented region based on a difference in contrast as described in Japanese Patent Laid-open Publication No. 2010-44069.

However, the present inventors found that the above-mentioned two methods had the following two problems.

The first problem is that the reflected light generated by vertically illuminating the cut surface with light and reflecting the light on the cut surface is specularly reflected light, but the embedding-substance portion on the cut surface cannot be a perfect mirror surface and therefore, it is difficult to receive only the specularly reflected light by 100%. That is, when irregular reflected light mixes, the unexposed biological-specimen portion appears dark, possibly leading to false detection of the unexposed biological-specimen portion.

The second problem is that, in the low-density biological specimen such as the adipose tissue, there is little difference in intensity between reflected light from the exposed biological-specimen portion and reflected light from the embedding-substance portion. Thus, there is little difference in luminance data and light and shade contrast data based on the luminance data between two portions.

An object of the present invention is to provide a sliced specimen preparing apparatus and a sliced specimen preparing method that can discriminate a specimen portion from an embedding-substance portion, on the surface of a specimen block, more clearly, to determine whether or not the area of the specimen portion is sufficient for the preparation of a sliced specimen.

A sliced specimen preparing apparatus according to the present invention is a sliced specimen preparing apparatus that prepares a sliced specimen by slicing a surface of a specimen block in which a specimen is embedded in an embedding substance. The apparatus includes a cutter configured to slice the surface of the specimen block, a surface exposure determination unit configured to determine whether or not the area of a specimen portion on the surface of the specimen block is sufficient for the preparation of the sliced specimen, a specimen block transporting unit configured to transport the specimen block, and a humidifying unit configured to humidify the surface of the specimen block. The surface exposure determination unit includes an irradiating unit configured to irradiate the surface of the specimen block with light, an imaging unit configured to receive reflected light from the humidified surface of the specimen block which is irradiated from the irradiating unit to acquire image data, an image data processing unit configured to discriminate the specimen portion on the surface of the specimen block from the embedding-substance portion based on the image data acquired by the imaging unit, and a controller configured to control the imaging unit, the irradiating unit, and the image data processing unit, and to determine whether or not the area of the specimen portion on the surface of the specimen block, the specimen portion being acquired by the image data processing unit, is sufficient for the preparation of the sliced specimen.

A sliced specimen preparing apparatus according to the present invention can discriminate a specimen portion from an embedding-substance portion, on the surface of a specimen block, more clearly, to determine whether or not the area of the specimen portion is sufficient for the preparation of a sliced specimen.

BRIEF DESCRIPTION OF THE DRAWINGS

The present invention will become readily understood from the following description of preferred embodiments thereof made with reference to the accompanying drawings, in which like parts are designated by like reference numeral, and in which.

DETAILED DESCRIPTION OF THE EMBODIMENTS

A sliced specimen preparing apparatus according to a first aspect of the present invention is a sliced specimen preparing apparatus that prepares a sliced specimen by slicing a surface of a specimen block in which a specimen is embedded in an embedding-substance, the apparatus including a cutter configured to slice the surface of the specimen block, a surface exposure determination unit configured to determine whether or not the area of a specimen portion on the surface of the specimen block is sufficient for the preparation of the sliced specimen, a specimen block transporting unit configured to transport the specimen block, and a humidifying unit configured to humidify the surface of the specimen block, wherein the surface exposure determination unit includes an irradiating unit configured to irradiate the surface of the specimen block with light, an imaging unit configured to receive reflected light from the humidified surface of the specimen block which is irradiated from the irradiating unit to acquire image data, an image data processing unit configured to discriminate the specimen portion on the surface of the specimen block from the embedding-substance portion based on the image data acquired by the imaging unit, and a controller configured to control the imaging unit, the irradiating unit, and the image data processing unit, and to determine whether or not the area of the specimen portion on the surface of the specimen block, the specimen portion being acquired by the image data processing unit, is sufficient for the preparation of the sliced specimen.

Moreover, in the first aspect, the imaging unit receives reflected light from the humidified surface of the specimen block to acquire image data containing luminance information, and the image data processing unit may discriminate the specimen portion on the surface of the specimen block from the embedding-substance portion based on light and shade contrast data acquired based on the luminance information in the image data, the luminance information being acquired by the imaging unit.

Further, in the first aspect, the controller of the surface exposure determination unit may control the specimen block transporting unit and the cutter.

Furthermore, when determining that the area of the specimen portion on the surface of the specimen block is not sufficient for the preparation of the sliced specimen, the controller causes the specimen block transporting unit to transport the specimen block to the cutter, the cutter to roughly cut the specimen block, and the controller causes the specimen block transporting unit to return the specimen block to the surface exposure determination unit, and the surface exposure determination unit determines whether or not the area of the specimen portion on the surface of the specimen block is sufficient for the preparation of the sliced specimen, and when determining that the area of the specimen portion on the surface of the specimen block is sufficient for the preparation of the sliced specimen, the controller causes the specimen block transporting unit to transport the specimen block to the cutter, and the cutter to slice the specimen block to prepare the sliced specimen.

A sliced specimen preparing method according to a second aspect of the present invention includes:

humidifying a surface of a specimen block in which a specimen is embedded in an embedding-substance;

discriminating the specimen portion on the humidified surface of the specimen block from the embedding-substance portion; and determining whether or not the acquired area of the specimen portion on the surface of the specimen block is sufficient for the preparation of a sliced specimen.

A sliced specimen preparing method according to a third aspect of the present invention is a sliced specimen preparing method that prepares a sliced specimen by slicing a surface of a specimen block in which a specimen is embedded in an embedding-substance with a cutter, the method includes:

slicing the surface of the specimen block in which specimen is embedded in the embedding-substance with the cutter;

discriminating the specimen portion on the surface of the specimen block from the embedding-substance portion;

humidifying the surface of the specimen block between the slicing step and the determining step; and determining whether or not the acquired area of the specimen portion on the surface of the specimen block is sufficient for the preparation of the sliced specimen.

From the second aspect or the third aspect, the step of discriminating the specimen portion on the surface of the specimen block from the embedding-substance portion may include:

irradiating the surface of the specimen block with light;

receiving reflected light from the surface of the specimen block which is irradiated to acquire image data containing luminance information; and discriminating the specimen portion on the surface of the specimen block from the embedding-substance portion based on light and shade contrast data acquired based on the luminance information in the acquired image data.

A sliced specimen preparing apparatus and a sliced specimen preparing method in accordance with embodiments of the present invention will be described with reference to appended figures. The same members throughout the figures are given the same reference numerals.

(First Embodiment)

<Sliced Specimen Preparing Apparatus>

Figure 5:
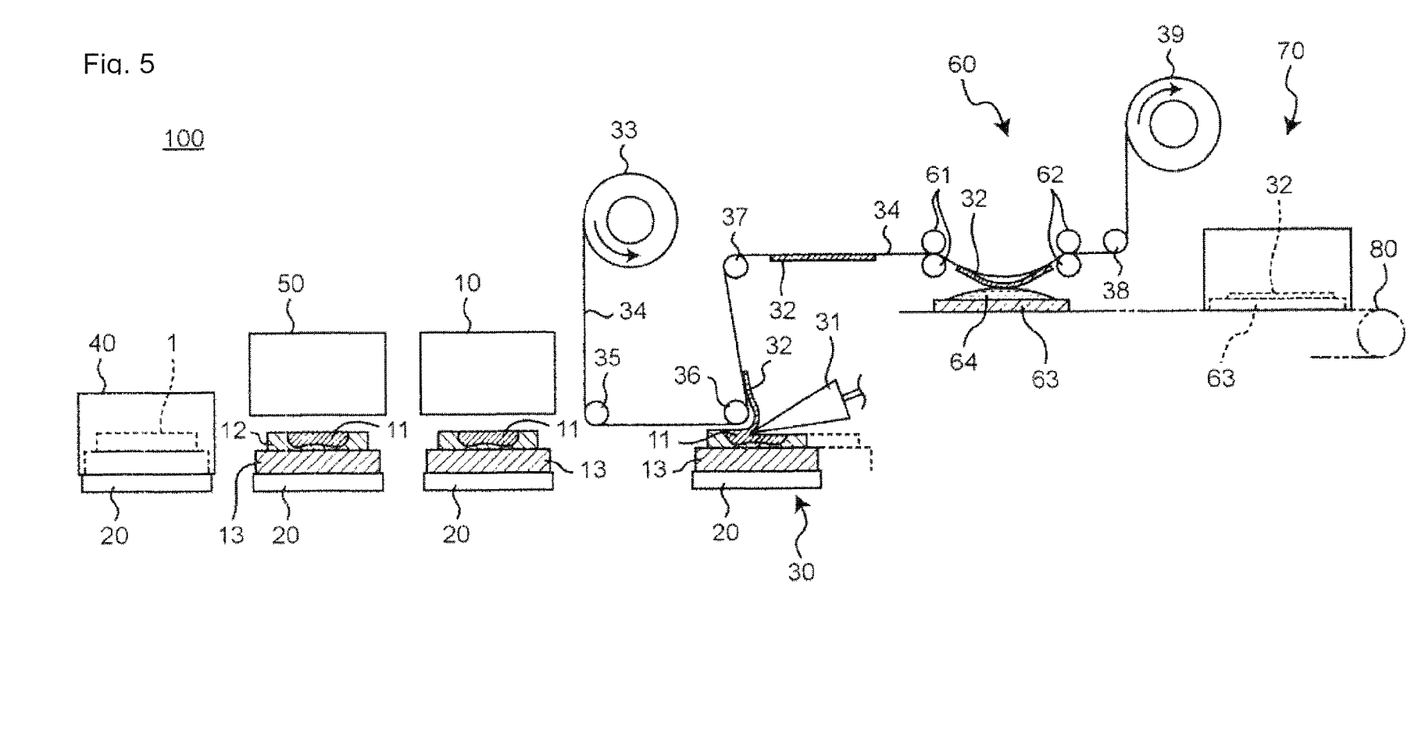
FIG. 5 is a schematic view showing configuration of the sliced specimen preparing apparatus in accordance with a first embodiment of the present invention.

FIG. 5 is a schematic view showing overall configuration of a sliced specimen preparing apparatus 100 in accordance with a first embodiment of the present invention. The sliced specimen preparing apparatus 100 may include at least a surface exposure determination unit 10 for a specimen block 1, a cutter 30 for slicing the surface of the specimen block 1, and a specimen block transporting unit 20 for transporting the specimen block 1. A controller 8 of the surface exposure determination unit 10 may control the specimen block transporting unit 20 and the cutter 30.

In the sliced specimen preparing apparatus 100, in the case where it is determined that the area of a portion of a specimen 11 on the surface of the specimen block 1 is not sufficient for the preparation of the sliced specimen, the specimen block transporting unit 20 transports the specimen block 1 to the cutter 30 to roughly cut the specimen block 1 and then, the specimen block transporting unit 20 returns the specimen block 1 to the surface exposure determination unit 10, and the surface exposure determination unit 10 determines whether or not the portion of a specimen 11 on the surface of the specimen block 1 is sufficient for the preparation of the sliced specimen. In contrast, in the case where it is determined that the area of the portion of a specimen 11 on the surface of the specimen block 1 is sufficient for the preparation of the sliced specimen, the specimen block transporting unit 20 transports the specimen block 1 to the cutter 30, and the cutter 30 slices the specimen block 1 to prepare the sliced specimen.

<Surface Exposure Determination Unit for Specimen Block>

Figure 1:
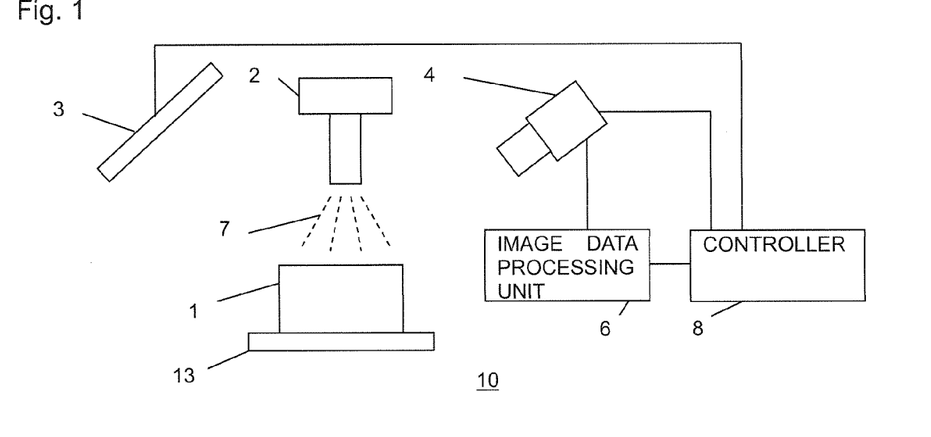
FIG. 1 is a schematic view showing configuration of a surface exposure determination unit for a specimen block in a sliced specimen preparing apparatus in accordance with a first embodiment of the present invention.

FIG. 1 is a schematic view showing configuration of the surface exposure determination unit 10 for the specimen block in the sliced specimen preparing apparatus 100 in accordance with the first embodiment of the present invention. The surface exposure determination unit 10 for the specimen block for preparing the sliced specimen includes a humidifying unit 2, an irradiating unit 3, an imaging unit 4, an image data processing unit 6, and the controller 8. The irradiating unit 3 irradiates the surface of the specimen block 1, in which the specimen 11 is embedded in an embedding-substance 12, with light. The imaging unit 4 receives reflected light from the surface of the specimen block 1 which is irradiated from the irradiating unit 3 to acquire image data containing luminance information. The image data processing unit 6 discriminates the portion of the specimen 11 on the surface of the specimen block 1 from the portion of the embedding-substance 12 based on the light and shade contrast data acquired by binarizing the luminance information in the image data in the imaging unit 4. The controller 8 controls the irradiating unit 3, the imaging unit 4, and the image data processing unit 6, and determines whether or not the area of the portion of the specimen 11 on the surface of the specimen block 1, which is acquired by the image data processing unit 6, is sufficient for the preparation of the sliced specimen.

Figure 2A:
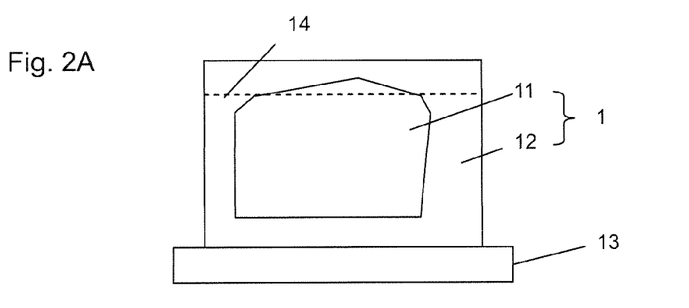
FIG. 2A is a cross-sectional view of the specimen block before rough cutting when viewed from the front.
Figure 2B:
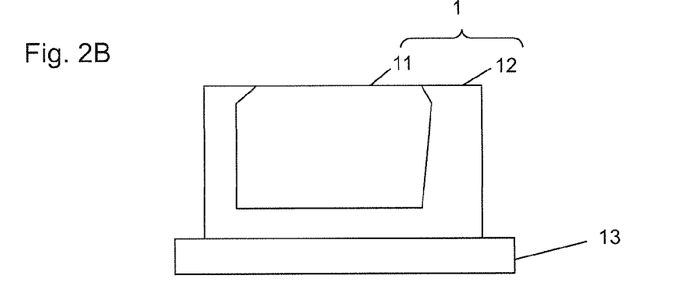
FIG. 2B is a cross-sectional view of the specimen block after rough cutting when viewed from the front.
Figure 2C:
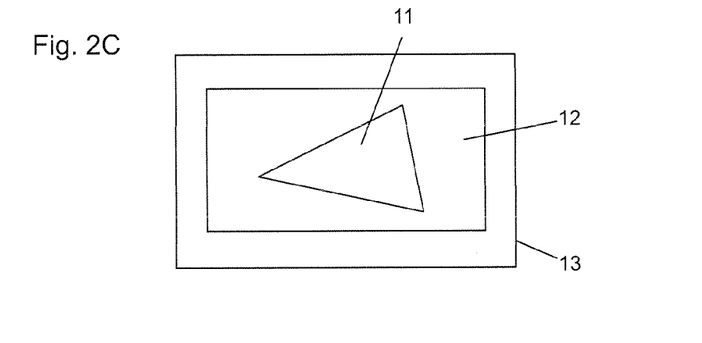
FIG. 2C is a plan view of the specimen block after rough cutting.

FIGS. 2A to 2C are schematic views showing configuration of the specimen block 1. FIG. 2A is a cross-sectional view of the specimen block 1 before rough cutting when viewed from the front, FIG. 2B is a cross-sectional view of the specimen block 1 after rough cutting when viewed from the front, and FIG. 2C is a plan view of the specimen block 1. The specimen block 1 is formed, for example, by embedding (imbedding) the biological specimen 11 or the like in the embedding-substance 12 such as paraffin. When used, the specimen block 1 is placed on a specimen table 13. When the specimen block 1 is cut with its surface being dried, it is hard to acquire a good slice, for example, because the cross unit of the specimen becomes napped. Moreover, the specimen block 1 is easy to be expanded or contracted by a minute change in temperature, disadvantageously causing irregular thickness of the slice at slicing. For this reason, a cooler and a humidifier not shown are provided to maintain a uniform temperature (for example, in the range of 10° C. to 25° C.) and a uniform humidity. The temperature and the humidity may be appropriately set according to the types of the specimen 11 used as the specimen block 1 and the embedding-substance 12.

In the surface exposure determination unit 10 for the specimen block for preparing the sliced specimen, the surface of the specimen block 1 is previously humidified to add moisture 7 to the portion of the specimen 11 on the surface of the specimen block 1 such that the portion of the specimen 11 has a lower luminance of specularly reflected light than the portion of the embedding-substance 12, and the portion of the specimen 11 on the surface of the specimen block 1 can be discriminated from the portion of the embedding-substance 12 based on the light and shade contrast data acquired by binarizing the luminance information in the image data acquired by the imaging unit 4. That is, by adding moisture to the portion of the specimen 11 on the surface of the specimen block 1 to decrease the luminance of specularly reflected light, a contrast difference between the specularly reflected light from the portion of the specimen 11 with added moisture and the specularly reflected light from the portion of the embedding-substance 12 can be increased. This enables distinct discrimination of the portion of the specimen 11 on the surface of the specimen block 1 from the portion of the embedding-substance 12. Thus, since it can be determined whether or not the portion of the specimen 11 sufficiently appears on the surface of the specimen block 1, surface exposure of the specimen block 1 can be performed in the preparation of the sliced specimen. When it is determined that the portion of the specimen 11 does not sufficiently appears on the surface of the specimen block 1, the surface of the specimen block 1 is roughly cut, for example, up to a surface 14 shown in FIG. 2A to perform surface exposure of the specimen block 1 again.

Each member constituting the surface exposure determination unit 10 for the specimen block for preparing the sliced specimen will be described below.

<Humidifying Unit>

Any humidifying unit that can humidify the surface of the specimen block 1 may be adopted. The humidifying unit 2 may be an atomizer for adding the moisture 7 in a mist form to the surface of the specimen block 1. Alternatively, the humidifying unit 2 may be a medium (for example, sponge and fabric) that can be in contact with the surface of the specimen block 1 and contains moisture. The humidifying unit 2 may be a high-humidity atmosphere box that can put the specimen block 1 into a high-humidity atmosphere. Although a humidifying unit that can put the entire device into the high-humidity atmosphere may be used, it is substantially difficult to keep the humidity of the entire device uniform. In addition, in cutting the specimen block, the image data of the cut surface is required, and it takes a long time to sufficiently humidify the cut surface, so it takes much time to acquire the image data. That is, it takes long time to determine whether or not the area of the specimen portion on the surface of the specimen block is sufficient for the preparation of the sliced specimen. Accordingly, it is preferred to humidify the surface of the specimen block (the surface of the specimen after slicing) with a humidifier capable of performing spot humidification, such as an atomizer, in a period from cutting the surface of the specimen block to acquirement of the image data. The humidifying unit 2 is preferably provided between the cutter 30 and the surface exposure determination unit 10, or in the surface exposure determination unit 10. In particular, by providing the humidifier such as the atomizer in the surface exposure determination unit 10, the humidification time can be shortened. Although the humidifying unit 2 is provided above the specimen block 1 in FIG. 1, the present invention is not limited to this. For example, the humidifying unit may humidify the surface in a direction vertical to the plane in FIG. 5 between the surface exposure determination unit 10 and the cutter 30. It is preferred to provide a spot humidifier such as the atomizer in the cutter 30 or between the cutter 30 and the surface exposure determination unit 10 to humidify the surface before slicing with the cutter 30 as well as after the slicing. In this case, the humidification effects before slicing and after slicing can be obtained with one humidifier. Preferably, the humidifying unit 2 can allow the portion of the specimen 11 on the surface of the specimen block 1 to absorb moisture at a high humidity (50 to 100%). In particular, the humidifying unit 2 can preferably humidify the surface in a short time by spraying or contacting of moisture. As described above, the humidifying unit 2 can add the moisture 7 to the portion of the specimen 11 on the surface of the specimen block 1 to decrease the luminance of the specularly reflected light from the portion of the specimen 11. As a result, the contrast difference between the specularly reflected light from the portion of the specimen 11 with added moisture and the specularly reflected light from the portion of the embedding-substance 12 can be increased.

<Irradiating Unit>

Any irradiating unit 3 that can irradiate the surface of the specimen block 1 with light may be adopted. For example, one or more monochrome LEDs may be used. A white light source may be used. A surface light source or a line light source may be used as the irradiating unit 3. In the case of using the line light source as the irradiating unit 3, a line sensor as the imaging unit 4 should be used to scan the surface of the specimen block 1 while keeping positions of the light source and the sensor with respect to each other. This is an only example, and does not limit the scope of the irradiating unit 3.

<Imaging Unit>

Any imaging unit 4 that can acquire the image data containing the luminance information may be adopted. The imaging unit may be a CCD camera. The imaging unit 4 may be an area camera or a line sensor. This is an only example, and does not limit the scope of the imaging unit 4.

<Image Data Processing Unit and Controller>

Any image data processing unit 6 that has a function of discriminating the portion of the specimen 11 on the surface of the specimen block 1 from the portion of the embedding-substance 12 based on the acquired image data may be adopted. Any controller 8 that controls the irradiating unit 3, the imaging unit 4, and the image data processing unit 6, and has a function of determining whether or not the area of the portion of the specimen 11 on the surface of the specimen block 1, which is acquired by the image data processing unit 6, is sufficient for the preparation of the sliced specimen may be adopted. The image data processing unit 6 and the controller 8 may be separated in terms of function for convenience, but may be integrated with each other. For example, a personal computer may be used as the image data processing unit 6 and the controller 8. The personal computer only needs to have necessary members including CPU, ROM, RAM, and HDD (memory), an input unit such as keyboard and mouse, a display unit, and input/output units.

<Cutter>

The cutter 30 performs rough cutting for surface exposure of the specimen block 1 and main cutting for the preparation of the sliced specimen.

In rough cutting, the surface of the specimen block 1 is cut by a predetermined thickness and then, the specimen block 1 is returned to the surface exposure determination unit 10 to make a surface exposure determination.

In main cutting, the surface of the specimen block 1 is sliced with a cutter 31 to prepare a sliced specimen 32. The prepared sliced specimen 32 is adhered to a carrier tape 34 supplied from a supply reel 33. In this case, humidification enables good adhesion of the sliced specimen 32 to the carrier tape 34. The carrier tape 34 is wound from a supply tape 33 by a take-up reel 39 through guide rollers 35, 36, 37, and 38. The cutter may be provided with a height adjustment mechanism.

<Specimen Block Transporting Unit>

Any specimen block transporting unit 20 that transports the specimen block 1 at least between the surface exposure determination unit 10 and the cutter 30 may be adopted.

As shown in FIG. 5, the sliced specimen preparing apparatus 100 may include a specimen block storage unit 40, a position adjustment unit 50, a transferring unit 60, an extending unit 70, and a slide glass transporting unit 80 in addition to the surface exposure determination unit 10, the cutter 30, and the specimen block transporting unit.

<Specimen Block Storage Unit>

The specimen block storage unit 40 removably stores the plurality of specimen blocks 1.

<Position Adjustment Unit>

The position adjustment unit 50 adjusts the inclination and the height of the surface of the specimen block 1.

<Transferring Unit>

The transferring unit 60 includes a pair of guide rollers 61 disposed in the upstream side of a travelling path of the carrier tape 34 and a pair of guide rollers 62 disposed in the downstream side of the travelling path. In the transferring unit 60, for example, a part of the carrier tape 21, to which the sliced specimen 32 is adhered, is held between the pair of guide rollers 61 and the pair of guide rollers 62, and the pair of guide rollers 62 or the pair of guide rollers 61 are moved downward in this state, thereby warping the carrier tape 21 downward. Thereby, the sliced specimen 32 is brought into contact with an upper surface of a slide glass 63, onto which an adhesive liquid 64 is supplied, to transfer the sliced specimen 32 on the upper surface of the slide glass 63. The slide glass on which the slice is transferred is referred to as slide glass having the slice.

<Extending Unit>

The extending unit 12 includes a heating plate (not shown) and applies first heating (for example, in the range of about 40° C. to 60° C., and for a few seconds to a few dozens of seconds) to the slide glass 63 having the slice, which is mounted on the heating plate (not shown) by the slide glass transporting unit 80, to extend wrinkles of the sliced specimen 32, thereby increasing the adhesive force of the sliced specimen 32 to the slide glass 63. After that, the extending unit 12 further applies second heating (for example, at 40° C. and for a few hours) to completely evaporate moisture on the slide glass 63 having the slice, thereby tightly fixing the sliced specimen 32 to the slide glass 63.

<Method of Determining Surface Exposure of Specimen Block>

Figure 3:
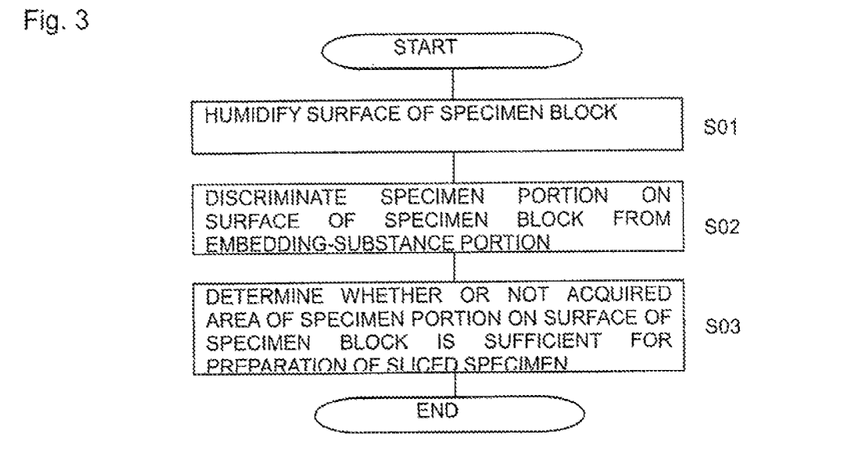
FIG. 3 is a flow chart of a method of determining surface exposure of the specimen block in a sliced specimen preparing method in accordance with the first embodiment of the present invention.

FIG. 3 is a flow chart of a method of determining surface exposure of the specimen block in the sliced specimen preparing method in accordance with the first embodiment. The method of determining surface exposure of the specimen block in the sliced specimen preparing method will be described below with reference to FIG. 3.

(a) The surface of the specimen block 1 is humidified (S01). Preferably, the surface is humidified so as to cause the portion of the specimen 11 on the surface of the specimen block 1 to absorb moisture with a high humidity (50 to 100%). For example, preferably, the surface of the specimen block 1 is spot-humidified with the moisture 7 in a mist form in a short time by using the atomizer.

(b) The portion of the specimen 11 on the surface of the specimen block 1 is discriminated from the portion of the embedding-substance 12 (S02). Details of Step S02 are shown in a flow chart of FIG. 4.

(c) It is determined whether or not the area of the obtained portion of the specimen 11 on the surface of the specimen block 1 is sufficient for the preparation of the sliced specimen (S03). Whether or not the area of the portion of the specimen 11 is sufficient for the preparation of the sliced specimen may be determined based on whether or not the area is a preset area or more. In the case where the whole of the surface of the specimen block 1, that is, the area of the inspected scope is previously found, whether or not the area of the portion of the specimen 11 is sufficient for the preparation of the sliced specimen may be determined based on the ratio of the area of the portion of the specimen 11 to the area of the inspected range. Further, in the case where the area of a maximum projected region of the specimen 11 in the specimen block 1 is previously found or can be estimated, whether or not the area of the portion of the specimen 11 is sufficient for the preparation of the sliced specimen may be determined based on the ratio of the portion of the specimen 11 to the area of the maximum projected region of the specimen 11.

Figure 4:
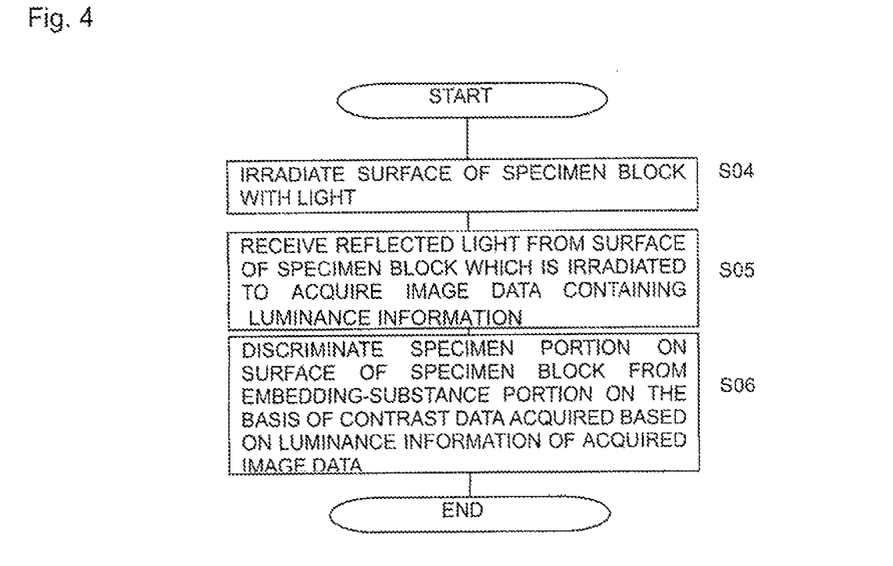
FIG. 4 is a flow chart showing details of a step of discriminating an acquired specimen portion on the surface of the specimen block from an embedding-substance portion, in the flow chart of FIG. 3.

FIG. 4 is a flow chart showing details of a step (S02) of discriminating the portion of the specimen 11 on the surface of the specimen block 1 from the portion of the embedding-substance 12 in FIG. 3.

(b-1) The surface of the specimen block 1 is irradiated with light (S04). In this case, for example, it is preferred to irradiate the surface with light from a position where the imaging unit 4 receives specularly reflected light.

(b-2) Reflected light from the surface of the specimen block 1 which is irradiated is received to obtain image data containing luminance information (S05). The received reflected light is preferably, specularly reflected light as described above.

(b-3) The portion of the specimen 11 on the surface of the specimen block 1 is discriminated from the portion of the embedding-substance 12 based on the light and shade contrast data acquired based on the acquired luminance information in the image data (S06). Describing in detail, the light and shade contrast data is acquired by binarizing the luminance information.

As described above, since the surface of the specimen block 1 is humidified (S01), the moisture 7 can be added to the portion of the specimen 11 on the surface to decrease the luminance of the specularly reflected light from the portion of the specimen 11. This is due to that, with the biological specimen 11, the tissues of the embedded biological specimen 11 easily absorb moisture, and the portion of the biological specimen 11 with moisture has a lower luminance of specularly reflected light than that before absorption of moisture. For this reason, the contrast difference between the specularly reflected light from the portion of the specimen 11 with added moisture and the specularly reflected light from the portion of the embedding-substance 12 can be increased. Thus, as compared to the case where moisture is not added as conventional, the portion of the specimen 11 on the surface of the specimen block 1 can be discriminated from the portion of the embedding-substance 12 more clearly.

According to the sliced specimen preparing method, the portion of the specimen 11 on the surface of the specimen block 1 can be discriminated from the portion of the embedding-substance 12 based on the light and shade contrast data acquired by binarizing the luminance information in the acquired image data. That is, by previously humidifying the surface of the specimen block and causing moisture to adhere to the portion of the specimen 11 on the surface to decrease the luminance of the specularly reflected light from the portion of the specimen 11, the contrast difference between the specularly reflected light from the portion of the specimen 11 and the specularly reflected light from the portion of the embedding-substance 12 can be increased. This enables distinct discrimination of the portion of the specimen 11 on the surface of the specimen block 1 from the portion of the embedding-substance 12. As a result, since it can be determined whether or not the portion of the specimen 11 sufficiently appears on the surface of the specimen block 1, in preparing the sliced specimen, the accuracy of determination of surface exposure of the specimen block 1 can be improved.

<Method of Preparing Slide Glass 63 Having Sliced Specimen 32>

Figure 6:
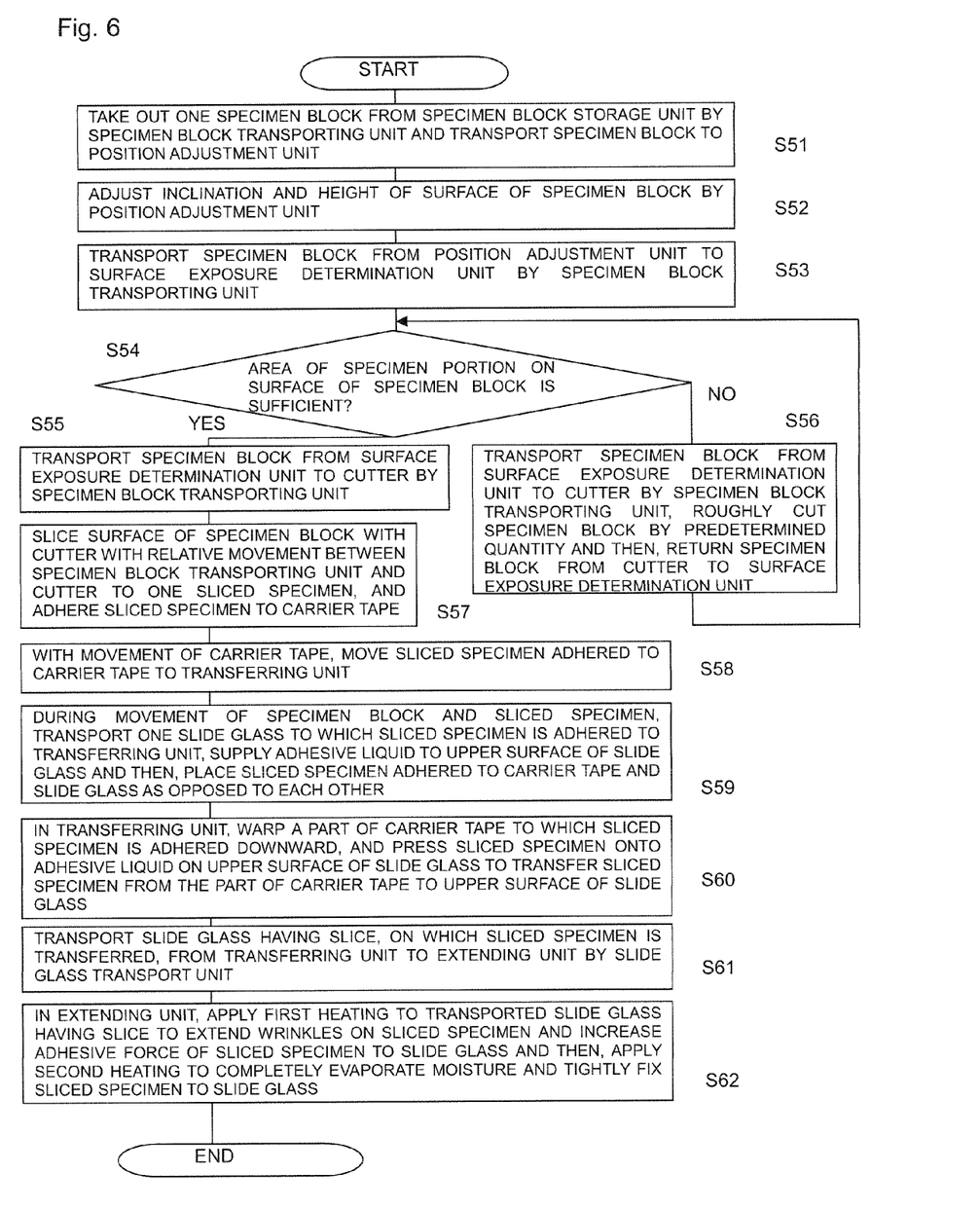
FIG. 6 is a flow chart showing a step of preparing a plurality of sliced specimens in the sliced specimen preparing apparatus in accordance with a first embodiment of the present invention.

FIG. 6 is a flow chart of a sliced specimen preparing method in accordance with the first embodiment of the present invention. The method of preparing the slide glass 63 having the sliced specimen 32 will be specifically described with reference to FIG. 6.

(a) First, the specimen block transporting unit 20 takes one specimen block 1 from the specimen block storage unit 40, and transports the specimen block to the position adjustment unit 50 (S51).

(b) The position adjustment unit 50 adjusts the inclination and the height of the surface of the specimen block 1 (S52).

(c) Subsequently, the specimen block transporting unit 20 transports the specimen block 1 from the position adjustment unit 50 to the surface exposure determination unit 10 (S53).

(d) As described above, the surface exposure determination unit 10 determines whether or not the area of the portion of the specimen 11 on the surface of the specimen block 1 is sufficient for the preparation of the sliced specimen (S54).

The surface exposure determination unit 10 may detect the area of the whole surface of the specimen block 1 before rough cutting in this device, as described in a below-mentioned second embodiment. The surface exposure determination unit 10 may detect the area of the maximum projected region of the specimen in the specimen block 1.

After rough cutting of a predetermined quantity, the surface exposure determination unit 10 determines whether or not the area of the portion of the specimen 11 on the surface of the specimen block 1, that is, the exposed portion of the specimen on the surface after slicing (after rough cutting) is sufficient for the preparation of the sliced specimen.

(e-1) In the case where it is determined that the area of the portion of the specimen 11 on the surface of the specimen block 1 is sufficient for the preparation of the sliced specimen, the specimen block transporting unit 20 transports the specimen block 1 from the surface exposure determination unit 10 to the cutter 30 (S55). That is, the procedure proceeds to the step of preparing an actual slice (main cutting).

(e-2) In the case where it is determined that the area of the portion of the specimen 11 on the surface of the specimen block 1 is not sufficient for the preparation of the sliced specimen, the specimen block transporting unit 20 transports the specimen block 1 from the surface exposure determination unit 10 to the cutter 30, and is roughly cut by the predetermined quantity. Then, the specimen block is returned from the cutter 30 to the surface exposure determination unit 10 (S56), and in Step S54, the surface exposure determination unit 10 determines whether or not the area of the portion of the specimen 11 on the surface of the specimen block 1 is sufficient for the preparation of the sliced specimen.

(f) In the cutter 30, the cutter 31 slices the surface of the specimen block 1 by means of relative movement between the specimen block transporting unit 20 and the cutter 31 to prepare one sliced specimen 32, and the sliced specimen 32 is adhered to the carrier tape 34 (S57).

(g) The sliced specimen 32 adhered to the carrier tape 34 is moved to the transferring unit 60 with movement of the carrier tape 34 (S58).

(h) During movement of the specimen block 1 and the sliced specimen 32, the slide glass transporting unit 80 transports one slide glass 63, to which the sliced specimen 32 is adhered, to the transferring unit 60, and the adhesive liquid 23 is supplied to the upper surface of the slide glass, and then, the sliced specimen 32 adhered to the carrier tape 34 is made opposed to the slide glass 63 (S59).

(i) In the transferring unit 60, a part of the carrier tape 34, to which the sliced specimen 32 is adhered, is warped downward, and the sliced specimen 32 is pressed onto the adhesive liquid 64 on the upper surface of the slide glass 63, thereby transferring the sliced specimen 32 from the part of the carrier tape 34 to the upper surface of the slide glass 63 (S60).

(j) The slide glass transporting unit 80 transports the slide glass 63 having the slice, onto which the sliced specimen 32 is transferred, from the transferring unit 60 to the extending unit 70 (S61).

(k) The extending unit 70 applies first heating (for example, in the range of about 40° C. to 60° C. and a few seconds to a few dozens of seconds) to the transferred slide glass 63 having the slice to extend wrinkles of the sliced specimen 32 and increase the adhesive force of the sliced specimen 32 to the slide glass 63. After that, the extending unit 70 further applies second heating (for example, at about 40° C. and a few hours) to completely evaporate moisture, thereby tightly fixing the sliced specimen 32 to the slide glass 63 (S62).

Thereby, the slide glass 63 having one sliced specimen 32 is prepared.

By transporting the specimen block 1 by the specimen block transporting unit 20 and automatically and continuously repeating the slicing operation any number of times as in the same manner, any number of sliced specimens 32 can be prepared.

(Second embodiment)

<Surface Exposure Determination Unit for Specimen Block>

Figure 7:
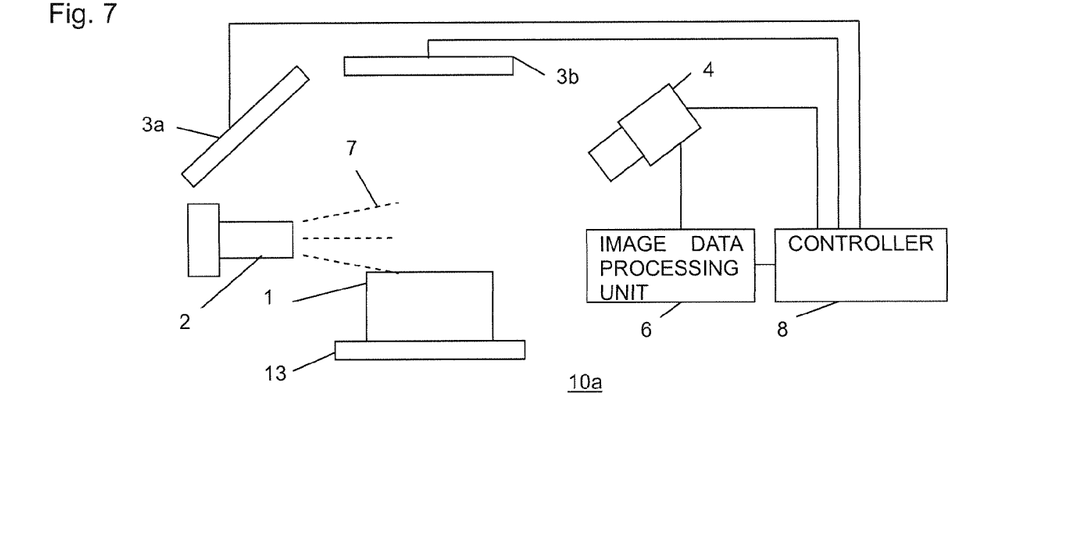
FIG. 7 is a schematic view showing configuration of the surface exposure determination unit for the specimen block in a sliced specimen preparing apparatus in accordance with a second embodiment of the present invention.

FIG. 7 is a schematic view showing the configuration of a surface exposure determination unit 10a for the specimen block in a sliced specimen preparing apparatus in accordance with a second embodiment. The surface exposure determination unit 10a for the specimen block is different from the surface exposure determination unit for the specimen block in the sliced specimen preparing apparatus in accordance with the first embodiment in that it includes two different irradiating units: a downward-light irradiating unit 3a and a diffused-light irradiating unit 3b. The downward-light irradiating unit 3a refers to a light source that irradiates the surface of the specimen block with light from a specularly reflected position with respect to the imaging unit 4. Although light irradiated from above in the direction vertical to the plane may be referred to as downward light, the downward light is not limited to this, and as shown in FIG. 7, may obliquely irradiate the plane. The diffused-light irradiating unit 3b refers to a light source that irradiates the surface of the specimen block with light from an irregular reflected position with respect to the imaging unit 4. Since the diffused-light irradiating unit 3b is provided, a maximum projected region (surrounded by a dotted line in FIG. 8B) Smax of the unexposed biological specimen 11 can be detected based on image data acquired using diffused light. Further, by making the amount of light received by the surface of the specimen block 1 from the downward-light irradiating unit 3a larger than usual amount, the whole region of the surface can be detected without discriminating the portion of the specimen 11 on the surface from the portion of the embedding-substance 12, and even when the size of the specimen block 1 changes, the inspected range can be recognized.

Figure 8A:
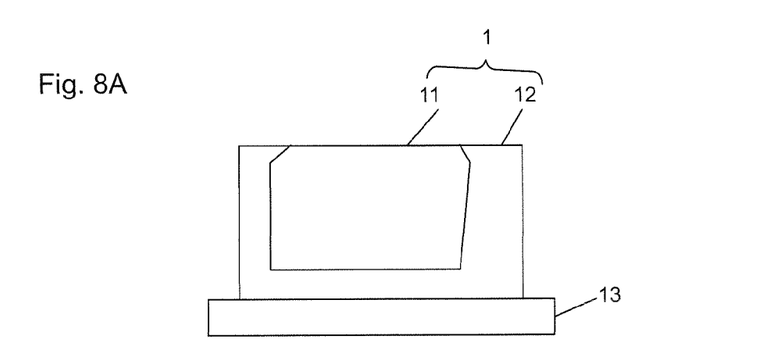
FIG. 8A is a cross-sectional view of the specimen block after rough cutting when viewed from the front.
Figure 8B:
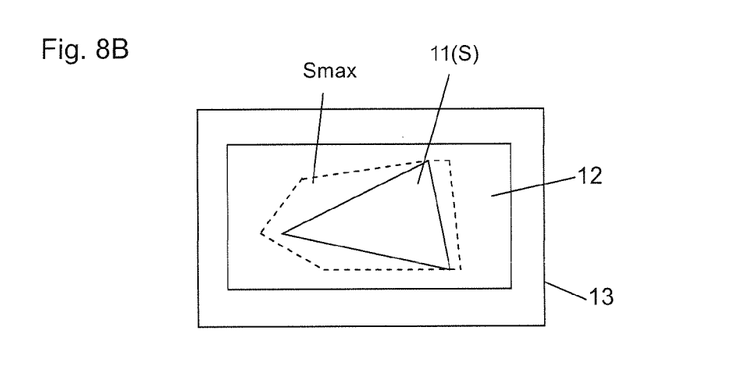
FIG. 8B is a plan view showing a maximum projected region of an unexposed specimen in the specimen block after rough cutting, which is represented by a dotted line.
Figure 14:
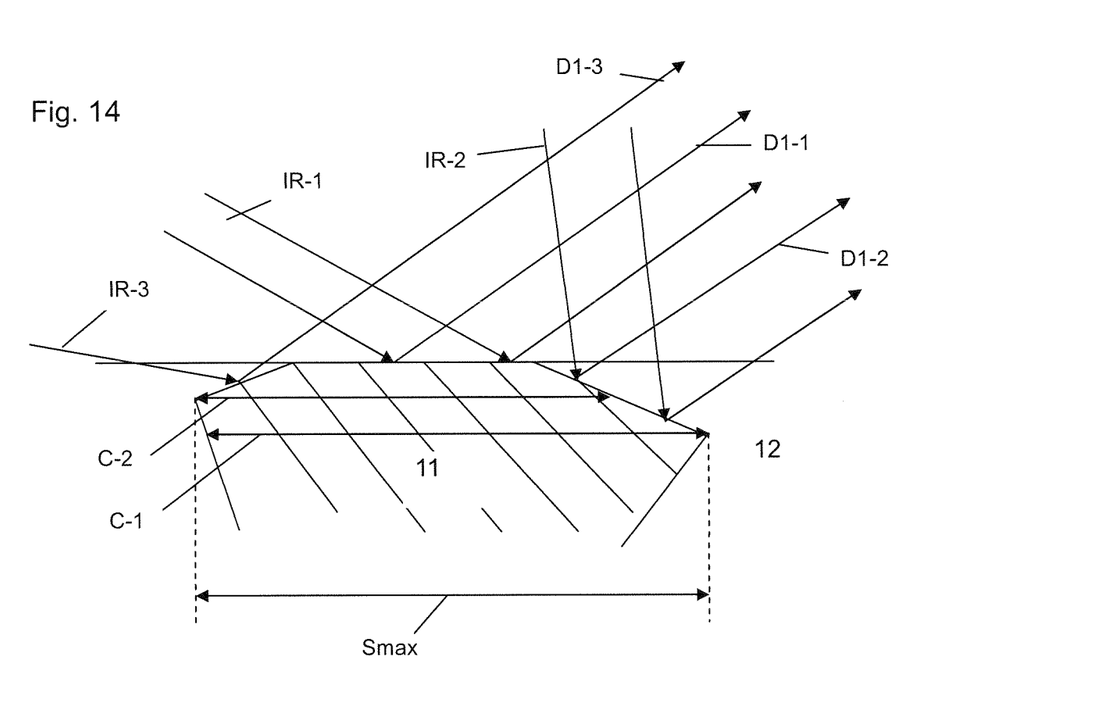
FIG. 14 is a schematic view for describing the principle that diffused light is used to detect the maximum projected region of the specimen in the specimen block in the flow chart of FIG. 11.

FIG. 8A is a cross-sectional view of the specimen block 1 after rough cutting when viewed from the front, and FIG. 8B is a plan view showing the maximum projected region of the unexposed specimen 11 in the specimen block 1 after rough cutting, which is represented by a dotted line. FIG. 14 is a schematic view for describing the principle that diffused light is used to detect the maximum projected region of the specimen 11 in the specimen block 1 in the flow chart of FIG. 11 described later. When only specularly reflected light DI-1 is received, it is difficult to detect the unexposed portion on the surface of the specimen block 1. The present inventors found that, as shown in cross-sectional view of FIG. 14, the area Smax of the maximum projected region could be detected by receiving diffused light DI-2 and DI-3 reflected from the unexposed specimen 11, which entered into the specimen block 1.

<Method of Determining Surface Exposure of Specimen Block>

Figure 9:
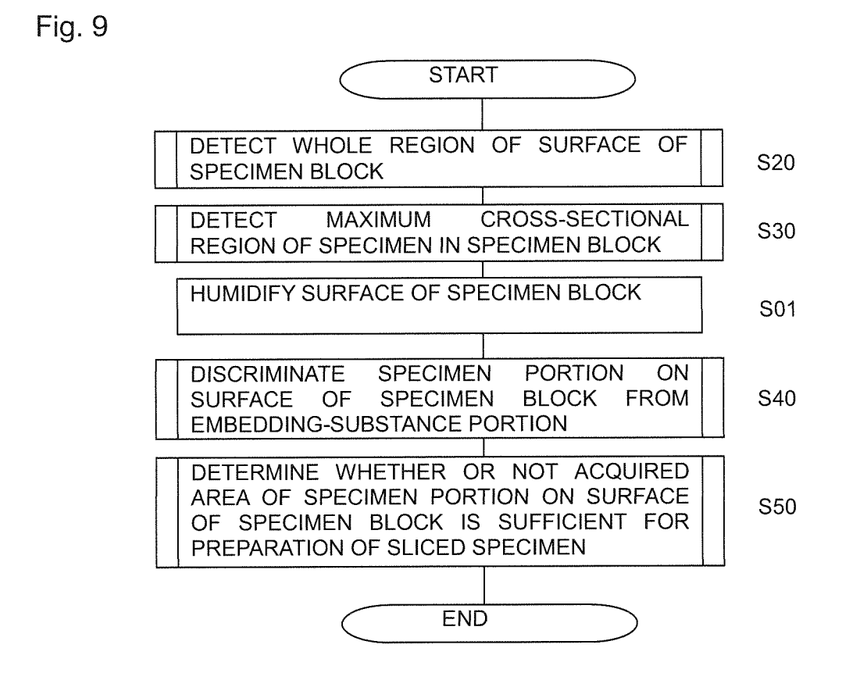
FIG. 9 is a flow chart of a method of determining surface exposure for specimen block in a sliced specimen preparing method in accordance with a second embodiment of the present invention.

FIG. 9 is a flow chart of a method of determining surface exposure of the specimen block in the sliced specimen preparing method in accordance with the second embodiment.

(a) The entire region of the surface of the specimen block 1 is detected (S20).

(b) The maximum projected region Smax of the specimen 11 in the cross unit parallel to the surface of the specimen block 1 is detected (S30). Generally, the (a) and (b) steps are performed before rough cutting in this device, and rough cutting is performed after the (b) step.

(c) The surface of the specimen block 1 in which the specimen 11 is embedded in the embedding-substance 12 is humidified (S01). This humidification is generally performed after rough cutting.

(d) The portion of the specimen 11 on the surface of the specimen block 1 is discriminated from the portion of the embedding-substance 12 (S40).

(e) It is determined whether or not the acquired area of the portion of the specimen 11 on the surface of the specimen block 1 is sufficient for the preparation of the sliced specimen (S50).

The (c) humidification step S01 is the same as the humidification step in first embodiment and thus, detailed description thereof is omitted. Details of steps other than the humidification step will be described below.

Figure 10:
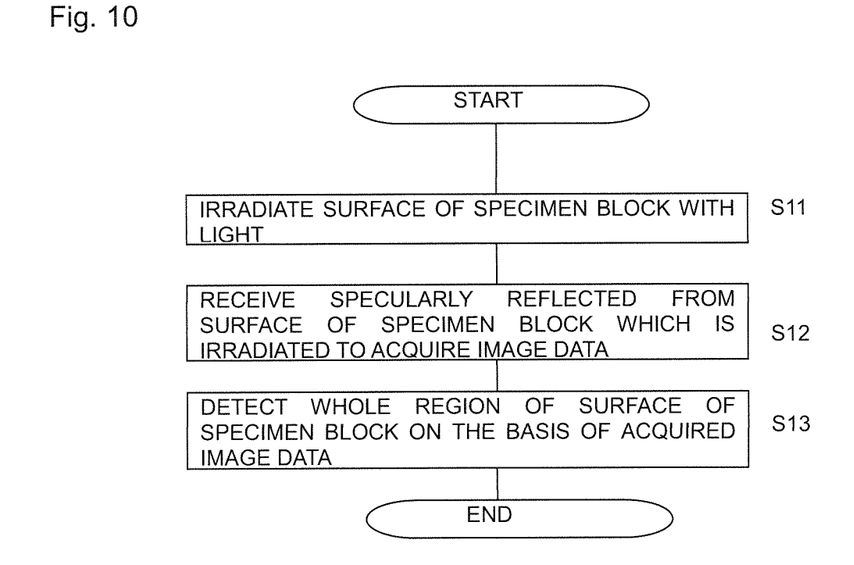
FIG. 10 is a flow chart showing details of a step of detecting the whole region of the surface of the specimen block, in the flow chart in FIG. 9.

FIG. 10 is a flow chart showing details of a step (S20) of detecting the whole region of the surface of the specimen block in FIG. 9.

(a-1) The surface of the specimen block is irradiated with light (S11). In this case, the downward-light irradiating unit 3a in FIG. 7 irradiates the surface with light. The amount of light from the downward-light irradiating unit 3a may be increased such that the amount of received light is larger than usual amount.

(a-2) Specularly reflected from the surface of the specimen block 1 which is irradiated is received to acquire image data (S12). In this case, in the previous step, the amount of light from the downward-light irradiating unit 3a may be increased, a light-receiving gain may be set to be high, or a light-receiving time may be extended. For example, the amount of received light may be more than as much as the usual amount of light. This is only a guidance, and may be any amount of received light as long as the light can illuminate the entire upper surface of the specimen block 1 more brightly than the specimen table 13. That is, the amount of received light is increased such that the entire surface becomes bright, that is, becomes white, without discriminating the portion of the specimen 11 from the portion of the embedding-substance 12. In this case, in the imaging unit 4, the amount of received light becomes saturated by the reflected light from the surface.

(a-3) The whole region of the surface of the specimen block is detected based on the acquired image data (S13). That is, the area of the upper surface of the specimen block 1 can be found based on the light and shade contrast data acquired by binarizing the luminance information in the acquired image data. In this case, the portion of the specimen 11 on the surface is not discriminated from the portion of the embedding-substance 12. The whole region of the surface becomes an inspected range. Thus, the inspected range can be recognized even when the size of the specimen block 1 changes.

Generally, the step (S20) of detecting the whole region of the surface of the specimen block is performed once before rough cutting in this device, but may be performed plural times as necessary.

Figure 11:
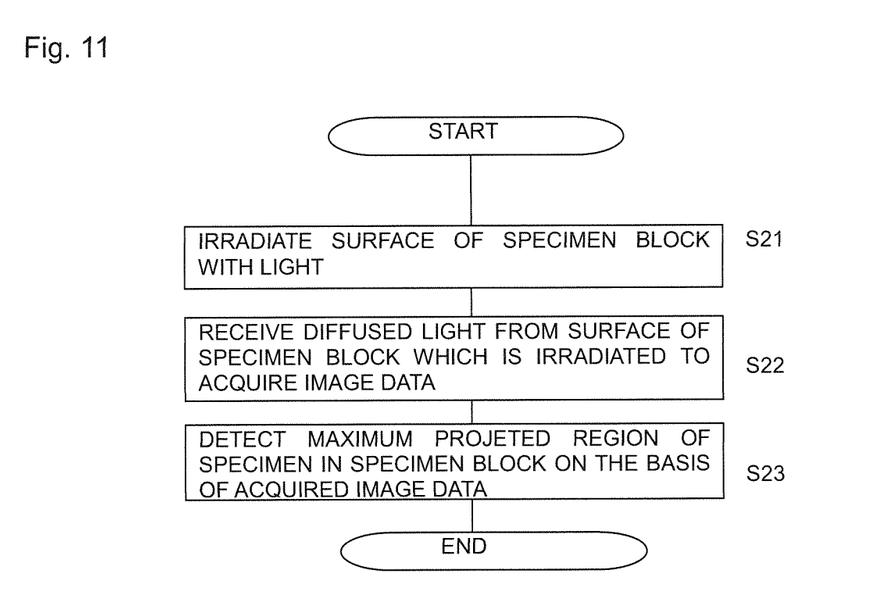
FIG. 11 is a flow chart showing details of a step of detecting a maximum projected region of the specimen in the specimen block, in the flow chart of FIG. 9.

FIG. 11 is a flow chart showing details of a step (S30) of detecting the maximum projected region of the specimen 11 in a cross unit parallel to the surface of the specimen block 1 in FIG. 9.

(b-1) The surface of the specimen block is irradiated with light of two or more colors having different wavelengths (S21). In this case, the diffused-light irradiating unit 3b in FIG. 7 irradiates the surface with light.

(b-2) Light irradiated and diffused from the surface of the specimen block is received to acquire image data (S22). In this case, as shown in FIG. 14, diffused light DI-2 and DI-3 can be received from the unexposed portion of the specimen 11 on the surface of the specimen block 1. In this case, a cross unit C-1 of the unexposed portion of the specimen 11, which is acquired from the diffused light DI-2, may be different from a cross unit C-2 of the unexposed portion of the specimen 11, which is acquired from the diffused light DI-3. That is, the maximum projected region Smax is not one cross unit, but refers to a region acquired by projecting the largest range of the specimen to the surface.

(b-3) The maximum projected region of the specimen 11 in the specimen block 1 is detected based on the acquired image data (S23). In this case, the unexposed portion of the biological specimen 11 as well as the portion of the biological specimen 11, which appears in the inspected range, are detected. Further, by using the image data acquired from diffused light, the maximum projected region of the unexposed biological specimen 11 can be detected. Generally, the step (S30) of detecting the maximum projected region of the specimen 11 in the cross unit parallel to the surface of the specimen block 1 is performed only once before rough cutting in this device, but may be performed plural times as necessary.

Figure 12:
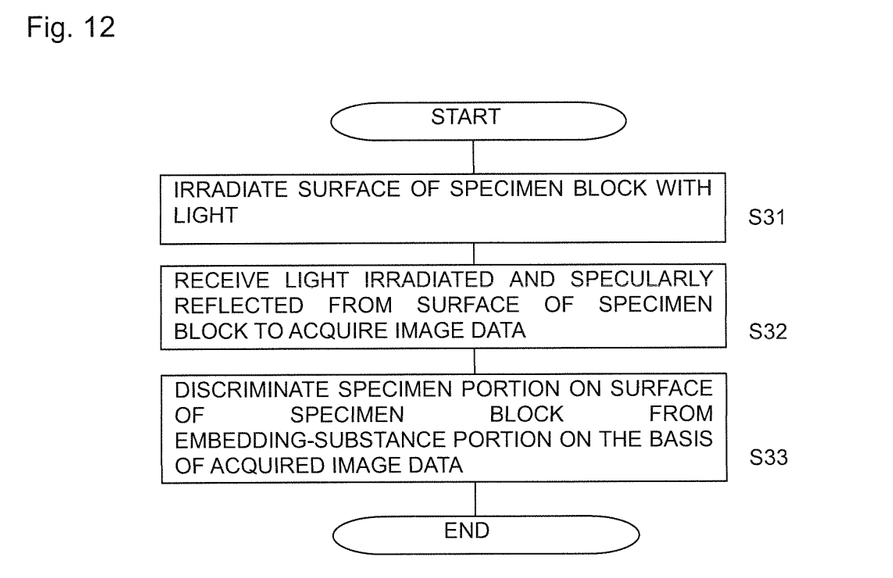
FIG. 12 is a flow chart showing details of a step of discriminating the specimen portion on the surface of the specimen block from the embedding-substance portion in the flow chart of FIG. 9.

FIG. 12 is a flow chart showing details of a step (S40) of discriminating the portion of the specimen 11 on the surface of the specimen block 1 from the portion of the embedding-substance 12 in FIG. 9.

(c-1) The surface of the specimen block 1 is irradiated with light (S31). In this case, the downward-light irradiating unit 3a in FIG. 7 irradiates the surface with light.

(c-2) Specularly reflected light from the surface of the specimen block 1 which is irradiated is received to acquire image data (S32). It is preferred that the amount of received light in this case is smaller than that in the step (S10) of detecting the whole region of the surface of the specimen block.

(c-3) Based on the acquired image data, the portion of the specimen 11 on the surface of the specimen block 1 is discriminated from the portion of the embedding-substance 12 (S33). In this case, the portion of the biological specimen 11 is discriminated from the portion of the embedding-substance 12 by using the light and shade contrast data acquired by binarizing the luminance information. Specifically, according to contrast caused by difference in the intensity of specularly reflected light, a "bright" portion is determined as the portion of the "embedding-substance", and a "dark" portion is determined as the portion of the "biological specimen".

Each of the steps is performed substantially after rough cutting of any quantity, but may be performed before initial rough cutting.

Figure 13:
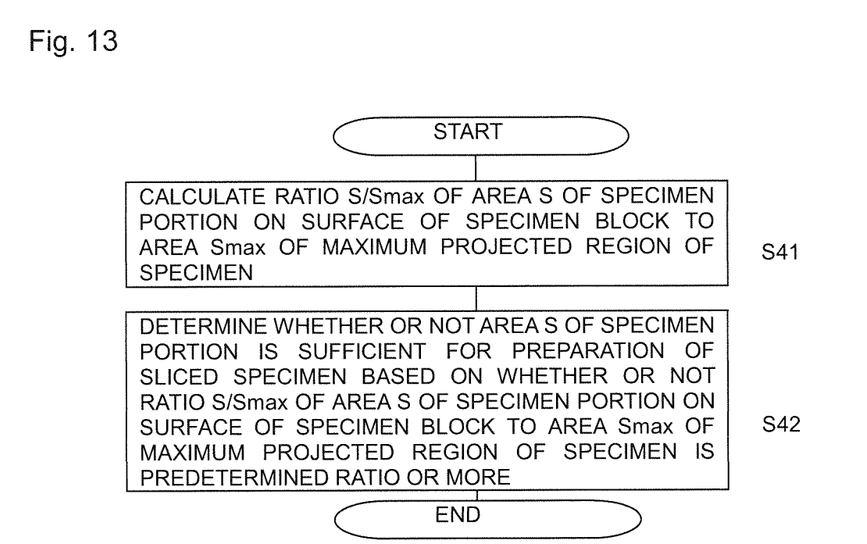
FIG. 13 is a flow chart showing details of a step of determining whether or not the area of the acquired specimen portion on the surface of the specimen block is sufficient for the preparation of the sliced specimen, in the flow chart of FIG. 9.

FIG. 13 is a flow chart showing specific contents of a step (S50) of determining whether or not the area of the acquired portion of the specimen 11 on the surface of the specimen block 1 in FIG. 9 is sufficient for the preparation of the sliced specimen.

(d-1) A ratio S/Smax of the area S of the portion of the specimen 11 on the surface of the specimen block 1 to the area Smax of the maximum projected region of the specimen 11 is calculated (S41).

(d-2) It is determined whether or not the area S of the portion of the specimen 11 is sufficient for the preparation of the sliced specimen, based on whether or not the ratio S/Smax of the area S to the area Smax of the maximum projected region of the specimen 11 is a predetermined ratio or more (S42).

When it is determined that the portion of the specimen 11 on the surface of the specimen block 1 is sufficient for the preparation of the sliced specimen, the procedure proceeds to the step of preparing an actual slice (main cutting). In contrast, when it is determined that the portion of the specimen 11 on the surface of the specimen block 1 is not sufficient for the preparation of the sliced specimen, after rough cutting of any quantity, Step S40 of discriminating the portion of the specimen 11 on the surface of the specimen block from the portion of the embedding-substance 12, and Step S50 of determining whether or not the area of the portion of the specimen 11 on the surface of the specimen block 1 is sufficient for the preparation of the sliced specimen are repeated.

The present invention is not limited to the above-mentioned embodiments, and may be implemented in other various modes.

In the sliced specimen preparing apparatus and the sliced specimen preparing method according to the present invention, by humidifying the surface of the specimen block, the luminance of the specimen portion on the surface is decreased to increase the contrast difference between the specularly reflected light from the portion of the specimen 11 with added moisture and the specularly reflected light from the portion of the embedding-substance 12. This enables distinct discrimination of the portion of the specimen 11 on the surface of the specimen block 1 from the portion of the embedding-substance 12. Since it can be determined whether or not the area of the specimen portion is sufficient for the preparation of the sliced specimen, the device and the method are suitable as sliced specimen preparing apparatus and method for preparing the sliced specimen used for physical and chemical specimen analysis and microscopic observation of biological specimens.

DESCRIPTION OF REFERENCE SIGNS 1 specimen block
2 humidifying unit
3 irradiating unit
4 imaging unit
6 image data processing unit
8 controller
10 surface exposure determination unit
11 specimen
12 embedding-substance
13 specimen table
20 specimen block transporting unit
30 cutter
31 cutter
32 sliced specimen
33 supply reel
34 carrier tape
35, 36, 37, 38 guide roller
39 take-up reel
40 specimen block storage unit
50 position adjustment unit
60 transferring unit
61, 62 guide roller
63 slide glass
64 adhesive liquid
70 extending unit
80 slide glass transporting unit
100 sliced specimen preparing apparatus

The invention claimed is:

1. A sliced specimen preparing apparatus that prepares a sliced specimen by slicing a surface of a specimen block in which a specimen is embedded in an embedding-substance, the apparatus comprising:
a cutter configured to slice the surface of the specimen block;
a surface exposure determination unit configured to determine whether or not the area of a specimen portion on the surface of the specimen block is sufficient for the preparation of the sliced specimen;
a specimen block transporting unit configured to transport the specimen block; and a humidifying unit configured to add moisture in a mist form to the surface of the specimen block, wherein
the surface exposure determination unit includes:
- an irradiating unit configured to irradiate the surface of the specimen block with light;
- an imaging unit configured to receive reflected light from humidified surface of the specimen block which is irradiated from the irradiating unit to acquire image data;
- an image data processing unit configured to discriminate the specimen portion on the surface of the specimen block from the embedding-substance portion based on the image data acquired by the imaging unit; and
- a controller configured to control the imaging unit, the irradiating unit, and the image data processing unit, and to determine whether or not the area of the specimen portion on the surface of the specimen block, the specimen portion being acquired by the image data processing unit, is sufficient for the preparation of the sliced specimen.

2. The sliced specimen preparing apparatus according to claim 1, wherein
the imaging unit receives reflected light from the humidified surface of the specimen block to acquire image data containing luminance information, and
the image data processing unit discriminates the specimen portion on the surface of the specimen block from the embedding-substance portion based on light and shade contrast data acquired based on luminance information in the image data, the luminance information being acquired by the imaging unit.

3. The sliced specimen preparing apparatus according to claim 1, wherein the controller of the surface exposure determination unit controls the specimen block transporting unit and the cutter such that,
when determining that the area of the specimen portion on the surface of the specimen block is not sufficient for the preparation of the sliced specimen, the controller causes the specimen block transporting unit to transport the specimen block to the cutter, the cutter roughly cuts the specimen block, and the controller causes the specimen block transporting unit to return the specimen block to the surface exposure determination unit, and the surface exposure determination unit determines whether or not the area of the specimen portion on the surface of the specimen block is sufficient for the preparation of the sliced specimen, and
when determining that the area of the specimen portion on the surface of the specimen block is sufficient for the preparation of the sliced specimen, the controller causes the specimen block transporting unit to transport the specimen block to the cutter, and the cutter slices the specimen block to prepare the sliced specimen.

4. The sliced specimen preparing apparatus according to claim 2, wherein the controller of the surface exposure determination unit controls the specimen block transporting unit and the cutter such that,
when determining that the area of the specimen portion on the surface of the specimen block is not sufficient for the preparation of the sliced specimen, the controller causes the specimen block transporting unit to transport the specimen block to the cutter, the cutter roughly cuts the specimen block, and the controller causes the specimen block transporting unit to return the specimen block to the surface exposure determination unit, and the surface exposure determination unit determines whether or not the area of the specimen portion on the surface of the specimen block is sufficient for the preparation of the sliced specimen, and
when determining that the area of the specimen portion on the surface of the specimen block is sufficient for the preparation of the sliced specimen, the controller causes the specimen block transporting unit to transport the specimen block to the cutter, and the cutter slices the specimen block to prepare the sliced specimen.

* * * * *